United States Patent [19]

Yellin et al.

[11] Patent Number: 4,696,933

[45] Date of Patent: Sep. 29, 1987

[54] GUANIDINE COMPOUNDS USEFUL AS HISTAMINE H2-ANTAGONISTS

[75] Inventors: Tobias O. Yellin, Fremont, Calif.; David J. Gilman, Tytherington, United Kingdom

[73] Assignees: ICI Americas Inc.; Imperial Chemical Industries PLC, United Kingdom

[21] Appl. No.: 701,012

[22] Filed: Feb. 12, 1985

Related U.S. Application Data

[62] Division of Ser. No. 353,423, Mar. 1, 1982, Pat. No. 4,496,564.

[30] Foreign Application Priority Data

Mar. 9, 1981 [GB] United Kingdom ............... 8107272

[51] Int. Cl.$^4$ .................. A01K 31/41; C07D 249/04; C07D 401/12
[52] U.S. Cl. .................. 514/275; 514/237; 514/238; 514/256; 514/318; 514/326; 514/332; 514/335; 514/340; 514/341; 514/342; 514/343; 546/192; 546/208; 546/193; 548/128; 548/130; 548/132; 548/133; 548/184; 548/194; 548/232; 548/236; 548/255; 548/265; 548/266; 548/337; 548/377
[58] Field of Search ............... 546/192, 208; 548/193, 548/337; 514/237, 238, 256, 275, 318, 326, 332, 335, 340, 341, 342, 343

[56] References Cited

U.S. PATENT DOCUMENTS

| | | | |
|---|---|---|---|
| 4,362,736 | 12/1982 | Hirata et al. | 548/193 |
| 4,451,463 | 5/1984 | Laye | 548/193 |
| 4,496,571 | 1/1985 | Yellin et al. | 548/232 |
| 4,570,000 | 2/1986 | Jones et al. | 548/193 |

OTHER PUBLICATIONS

Laye, Chem. Abst., 98-143463n.
Yellin et al, Chem. Abst., 98-89389c.
Hales et al, Chem. Abst., 101-110910h.
Imperial Chemical Industries PLC, Chem. Abst., 101-110911j.
Kirkland et al, Chem. Abst., 104-19576e.
Yamanouchi Pharmaceutical Co. Ltd., Chem. Abst., 96-68976k, eq. JP.81108777.
Hirata et al, Chemical Abstract, 94-13979w, eq. Ger. Offen. 3008056.

*Primary Examiner*—Donald G. Daus
*Assistant Examiner*—Cecilia Shen
*Attorney, Agent, or Firm*—Cushman, Darby & Cushman

[57] ABSTRACT

The invention relates to amide derivatives which are histamine H-2 antagonists and which inhibit gastric acid secretion. According to the invention there is provided a guanidine derivative of the formula I:

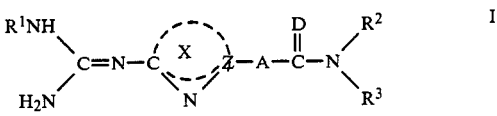

in which $R^1$ is a hydrogen or 1–10C alkyl, 3–8C cycloalkyl, 4–14C cycloalkyl, 3–6C alkenyl, 3–6C alkynyl, 1–6C alkanoyl, 6–10C aryl, 7–11C aralkyl or 7–11C aroyl, the aryl, aralkyl and aroyl radical being optionally substituted; ring X is a heterocyclic ring as defined in the specification; A is phenylene or 5–7C cycloalkylene, or a 1–8C alkylene into which is optionally inserted one or two groups; D is O or S; and $R^2$ and $R^3$ are hydrogen or a variety of radicals described in the specification: and the pharmaceutically-acceptable acid-addition salts thereof. Manufacturing processes and pharmaceutical compositions are also described.

9 Claims, No Drawings

GUANIDINE COMPOUNDS USEFUL AS HISTAMINE H2-ANTAGONISTS

This is a division of application Ser. No. 353,423, filed Mar. 1, 1982, now U.S. Pat. No. 4,496,564.

This invention relates to amide derivatives which are histamine H-2 antagonists and which inhibit gastric acid secretion.

It is postulated that the physiologically-active compound histamine, which occurs naturally within the animal body, is able to combine, in the course of exerting its activity, with certain specific receptors of which there are at least two distinct and separate types. The first has been named for the H-1 receptor (Ash and Schild, *Brit. J. Pharmac.* 1966, 27, 427) and the reaction of histamine at this receptor is blocked (antagonised) by classical "antihistamine" drugs such as mepyramine. The second histamine receptor has been named the H-2 receptor (Black et al., *Nature,* 1972, 236, 385) and the action of histamine at this receptor is blocked by drugs such as cimetidine. It is known that one of the results of the blockade of the action of histamine at the H-2 receptor is the inhibition of the secretion of gastric acid and a compound which possesses this ability is therefore useful in the treatment of peptic ulcers and other conditions caused or exacerbated by gastric acidity.

In UK Patent Application No. GB2052478A and Japanese Patent Application No. J56108777(Derwent Accession No. 74736 D/41) there are described histamine H-2 receptor antagonists which are 2-guanidinothiazole derivatives carrying a side chain in the 4-position to the end of which is attached a carbamoyl group.

It has now been discovered that certain other heterocycles carrying both an optionally-substituted guanidine group and a side chain to the end of which is attached an optionally substituted carbamoyl group are potent histamine H-2 receptor antagonists.

According to the invention there is provided a guanidine derivative of the formula I:

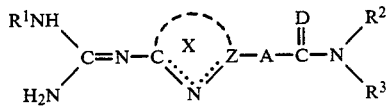

in which $R^1$ is a hydrogen atom or a 1–10C alkyl, 3–8C cycloalkyl, 4–14C cycloalkylalkyl, 3–6C alkenyl, 3–6C alkynyl, 1–6C alkanoyl, 6–10C aryl, 7–11C aralkyl or 7–11C aroyl radical, the aryl, aralkyl an aroyl radicals being optionally substituted on the aryl ring by one or two substituents selected from halogen atoms and 1–6C alkyl, 1–6C alkoxy, 1–6C alkylthio, trifluoromethyl, hydroxy and amino radicals;

in ring X the dotted line is a double bond on one side of the nitrogen atom and Z is a carbon or nitrogen atom such that ring X is a 5- or 6-membered aromatic heterocyclic ring which contains at least one nitrogen atom and may optionally contain one or two additional hetero atoms selected from oxygen, nitrogen and sulphur atoms, which heterocyclic ring may, where possible, carry one or two optional substituents, the optional substituents on ring X being selected from fluorine, chlorine and bromine atoms and 1–6C alkyl, 1–6C alkoxy, trifluoromethyl, hydroxy and amino radicals;

A is a phenylene or 5–7C cycloalkylene radical or a 1–8C alkylene chain which is optionally substituted by one or two 1–3C alkyl radicals and into which is optionally inserted, as part of the backbone of the chain, one or two groups selected from oxygen and sulphur atoms and NH, 1–6C N-alkyl, cis and trans vinylene, ethynylene, phenylene and 5–7C cycloalkylene radicals, provided that the shortest link between ring X and C=D is of at least 3 atoms, provided that when an optional insertion is made in chain A which results in the inserted group being directly attached to C=D the inserted group is other than an oxygen or sulphur atom or an NH or N-alkyl, radical, and provided that no two insertions selected from oxygen and sulphur atoms and NH and N-alkyl radicals are directly attached one to the other;

D is an oxygen or sulphur atom;

$R^2$ is a hydrogen atom or a hydroxy, amino, 1–6C alkylamino, 1–6C haloalkylamino, 1–6C alkanoylamino, 1–6C alkyl, 3–8C cycloalkyl, 4–12C cycloalkylalkyl, 2–6C alkenyl, 2–6C alkynyl, 1–6C haloalkyl, 1–6C alkoxy, 1–6C hydroxyalkyl, 2–10C alkoxyalkyl, 2–10C alkylthioalkyl, 1–6C aminoalkyl, 2–8C alkylaminoalkyl, 3–12C dialkylaminoalkyl, 2–8C alkanoylaminoalkyl, 8–14C aroylaminoalkyl, 3–10C alkoxycarbonylalkyl, 2–8C carbamoylalkyl, 6–10C aryl, 7–11C arylalkyl, heteroaryl or heteroarylalkyl radicals, wherein the heteroaryl part is a heterocyclic aromatic ring containing one, two or three heteroatoms selected from oxygen, nitrogen and sulphur atoms, wherein the alkyl part of the heteroarylalkyl radical is 1–6C and wherein, when $R^3$ is or contains an aryl or heteroaryl ring, that ring is optionally substituted by one or two groups selected from fluorine, chlorine, bromine and iodine atoms and 1–6C alkyl, 1–6C alkoxy, 1–6C alkylthio, 2–6C dialkylamino, 2–6C alkanoyl, trifluoromethyl, hydroxy and amino radicals;

$R^3$ is a hydrogen atom or $R^2$ and $R^3$ are joined to form, together with the nitrogen atom to which they are attached, a 5-, 6- or 7-membered saturated ring which optionally contains a double bond or an additional oxygen atom, NH or 1–6C alkyl radical;

provided that when $R^1$ is a hydrogen atom or an alkyl radical, ring X is a thiazole ring in which A is attached at the 4-position and A is an alkylene chain which has a single optional insertion of a sulphur atom, then $NR^2R^3$ is other than $NH_2$, NHOH or NH alkyl;

and the pharmaceutically-acceptable acid-addition salts thereof.

It is to be understood that, in the above formula I and throughout this specification, although the double bond in the guanidine residue attached to ring X has been inserted in a particular position, other tautomeric forms are possible, and this invention includes such tautomeric forms within its scope, both in terms of the compounds of the invention and in terms of the manufacturing processes. It is also to be understood that when A is or contains a cycloalkylene radical the groups attached to this radical may be in the cis or trans configuration. When A is or contains a cycloalkylene radical and/or when A is an alkylene chain substituted by one or two alkyl radicals the compound of the formula I will, in most instances, contain at least one asymmetric centre. In such cases the compound of the formula I will therefore exist in at least two enantiomeric forms, the precise number being determined by the number of asymmetric centres. The biological activity, as hereinafter defined, of these enantiomeric forms may differ, and it is therefore to be understood that this invention encompasses the racemate of the formula I, including any possible diastereoisomeric forms, and any enantiomeric form which possesses the disclosed biological activity, it being a matter of common general knowledge to one skilled in the art how to separate diastereoisomeric forms and how to separate a racemate into its enantiomers and determine the biological activity of each.

A particular value for $R^1$ is a hydrogen atom or a methyl, ethyl, propyl, isopropyl, butyl, cyclohexyl, cyclohexylmethyl, allyl, propargyl, acetyl, phenyl, benzyl or benzoyl radical, the phenyl, benzyl and benzoyl radicals being optionally substituted on the benzene ring by one or two substituents selected from fluorine, chlorine and bromine atoms and methyl, methoxy, methylthio, trifluoromethyl, hydroxy and amino radicals.

A particular value for ring X is an oxazole, thiazole, imidazole, 1,2,4-thiadiazole, 1,2,4-oxadiazole, 1,2,3-triazole, 1,2,4-triazole, pyrazole, pyrazine, pyridine, pyrimidine or 1,3,5-triazine ring, each being optionally substituted, where possible, by one or two substitutents selected from fluorine, chlorine and bromine atoms and methyl, methoxy, trifluoromethyl, hydroxy and amino radicals.

A particular value for —A— is a phenylene, cyclopentylene, cyclohexylene, trimethylene, tetramethylene, pentamethylene, thioethylene, thiotrimethylene, thiotetramethylene, thiopentamethylene, oxyethylene, oxytrimethylene, oxytetramethylene, methyleneethiomethylene, methyleneethioethylene, methylenethiopropylene, methyleneoxymethylene, methyleneoxyethylene, ethyleneoxyethylene, oxy-2-methylethylene, thiopropylenethiomethylene, oxyethyleneoxymethylene, iminoethylene, iminopropylene, vinylenepropylene, oxymethylenevinylene, 1,3-phenylene, 1,3-cyclopentylene, methylene-1,4-phenylene, ethyleneoxymethylene-1,4-phenylene, oxy-1,3-phenylenemethylene or thiomethyleneethynylenemethylene radical. These values for —A— are written reading from left to right in formula I such that the first named part of the radical is attached to ring X and the last named part of the radical is attached to C=D. Thus, for example, when —A— is a methylenethioethylene radical, the compound of the formula I contains the part structure II:

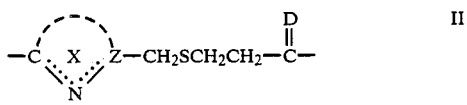

A particular value for $R^2$ is a hydrogen atom or a hydroxy, amino, methylamino, 2,2,2-trifluoroethylamino, acetylamino, methyl, cyclohexyl, cyclohexylmethyl, allyl, propargyl, 2,2,2-trifluoroethyl, methoxy, 2-hydroxyethyl, 2-methoxyethyl, 2,methylthioethyl, 2-aminoethyl, 2-methylaminoethyl, 2-dimethylaminoethyl, 2-acetylaminoethyl, 2-benzoylaminoethyl, methoxycarbonylmethyl, 2-carbamoylpropyl, phenyl, benzyl, heteroaryl and heteroarylmethyl, in the latter two of which the heteroaryl part is a furan, thiophene, pyrrole, thiazole oxazole, imidazole, thiadiazole, oxadiazole, triazole pyrazole, pyridine or pyrimidine ring, and wherein when $R^2$ is or contains a phenyl or heteroaryl ring, that ring is optionally substituted by one or two groups selected from fluorine, chlorine, bromine and iodine atoms and methyl, methoxy, methylthio, dimethylamino, acetyl, trifluoromethyl, hydroxy and amino radicals.

A particular value for the ring formed when $R^2$ and $R^3$ are joined is a pyrrolidine, piperidine, morpholine, piperazine or N-methylpiperazine ring.

The following are 7 preferred features of the guanidine derivative of the formula I. When any one of these features is taken, either singly or in combination, with the other general or particular features of the guanidine derivatives of the formula I listed above, there are obtained preferred sub-groups of compounds within the above general definition.

1. $R^2$ and $R^3$ are hydrogen atoms.
2. $R^1$ is a methyl, ethyl, propyl, isopropyl or allyl radical.
3. Ring X carries no optional substituent.
4. Ring X is a pyrazole, pyridine, pyrimidine in which A is attached at the 2-position, or 1,2,3-triazole ring.
5. Ring X is a pyrimidine in which A is attached at the 2-position or pyridine ring and A is a thiotrimethylene or tetramethylene radical.
6. Ring X is a pyrazole or 1,2,3-triazole ring and A is a tetramethylene radical.
7. D is an oxygen atom.

Specific compounds of the invention are set out in the Examples. The following is a group of preferred compounds:
4-(4-[2-propylguanidino]pyrimid-2-ylthio)butyramide (Example 1);
4-(4-[2-methylguanidino]pyrimid-2-ylthio)butyramide (Example 3);
4-(4-[2-isopropylguanidino]pyrimid-2-ylthio)butyramide (Example 4);
4-(6-[2-propylguanidino]pyrid-2-ylthio)butyramide (Example 7);
5-(4-[2-allylguanidino]-1,2,3-triazol-2-yl)valeramide (Example 8),
5-(4-[2-propylguanidino]-1,2,3-triazol-2-yl)valeramide (Example 9);
5-(3-[2-propylguanidino]pyrazol-1-yl)valeramide (Example 10);
and the pharmaceutically-acceptable acid-addition salts thereof.

A suitable pharmaceutically-acceptable acid-addition salt of the guanidine derivative of the formula I is, for example, a salt formed with hydrochloric, hydrobromic, phosphoric, sulphuric, acetic, citric or maleic acid.

The guanidine derivative of the invention may be manufactured by methods in which the actual chemical reactions involved are known in themselves. The following processes, $R^1$, $R^2$, $R^3$, A, D and ring X having the meanings stated above, unless indicated otherwise, are therefore provided as further features of the invention.

The process of the invention is characterised by:
(a) reaction of a compound of the formula III:

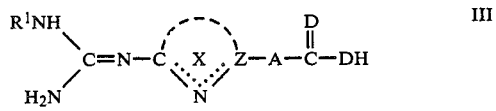

or an activated derivative thereof with a compound of the formula $R^2R^3NH$. The activated derivative may, for example, be an ester, for example a 1-6C alkyl ester for example a methyl or ethyl ester, or an acid halide, for example an acid chloride or acid bromide. Alternatively the activated derivative may be an anhydride, for example, a mixed anhydride. Particularly useful mixed anhydrides are those formed by reaction of the compound of the formula III with a chloroformate, for example ethyl chloroformate or isobutyl chloroformate. The reaction may be conducted in a diluent or solvent such as methanol, ethanol, methylene dichloride, tetrahydrofuran or dimethylformamide and the reaction may be accelerated or completed by the application of heat, for example by heating to the boiling point of the diluent or solvent. When the activated derivative is an acid halide it is advantageous to conduct the reaction in the presence of a base such as triethylamine and to use a non-alcoholic diluent or solvent.

(b) for those compounds in which $R^2$ and $R^3$ are hydrogen atoms and D is an oxygen atom, hydrolysis of a compound of the formula IV:

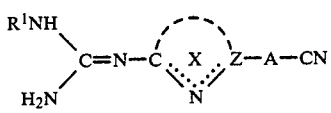

IV

The hydrolysis is preferably carried out by use of a strong mineral acid such as concentrated sulphuric acid or by use of hydrogen peroxide in a basic medium, for example in the presence of sodium hydroxide. When $R^1$ is a hydrogen atom, an acid labile protecting group attached to the nitrogen atom, for example a t-butyl radical, may also be removed during this process.

(c) construction of the guanidine radical attached to ring X by reaction of the appropriate thiourea, or a 1-6C S-alkyl (e.g. S-methyl) or S-benzyl derivative thereof, or a salt of such a derivative, with the appropriate amine. The guanidine radical in the compound of the formula I contains three nitrogen atoms each of which carries different substituents. The appropriate amine for use in this reaction may therefore be ammonia, an amine of the formula $R^1NH_2$ or an amine of the formula:

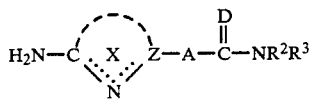

V

The reaction may be conducted using an excess of one of the reactants as a diluent or solvent, or an additional diluent or solvent, for example methanol or ethanol, may be added. In many cases it is advantageous to use a catalyst such as mercuric oxide, lead oxide or sodium hypochlorite. The reaction may be conducted at ambient temperature or it may be accelerated or completed by the application of heat, for example by heating to the boiling point of the diluent or solvent.

(d) for those compounds in which $R^1$ is a 3-10C alkyl radical, hydrogenation of the corresponding unsaturated derivative. In such an unsaturated derivative the radical corresponding to $R^1$ will have the same number and arrangement of carbon atoms as $R^1$ and will contain one or, where possible, more double and/or triple bonds. The reaction may be conducted in a diluent or solvent such as ethanol and in the presence of a catalyst such as a palladium on charcoal catalyst.

(e) construction of the guanidine radical attached to ring X by reaction of the appropriate cyanamide with the appropriate amine. Since the guanidine radical in the compound of the formula I contains only one unsubstituted nitrogen atom there are two appropriate amines, namely the amine of the formula $R^1NH_2$ or of the formula V given above.

(f) for those compounds in which the group inserted into A is an oxygen or sulphur atom or an NH or N-alkyl radical, reaction of a compound of the formula VI or VII:

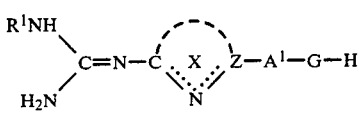

VI

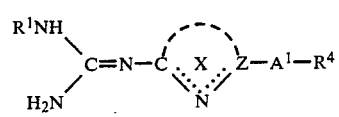

VII with a compound of the formula VIII or IX respectively:

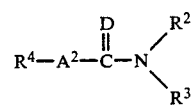

VIII

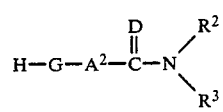

IX in which G is an oxygen or sulphur atom or an NH or N-alkyl radical, $R^4$ is a displaceable radical and $A^1$ and $A^2$ are fragments of A, including direct bonds, and are such that $A^1$—G—$A^2$ falls within the definition of A given above. $R^4$ is, for example, a halogen atom, for example a chlorine, bromine or iodine atom. When $R^4$ is directly attached to ring X $R^4$ may, for example, be a methylsulphinyl or methylsulphonyl radical.

(g) for those compounds in which Z is a nitrogen atom, reaction of a compound of the formula X:

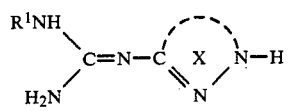

X with a compound of the formula XI:

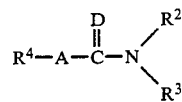

XI in which $R^4$ is a displaceable radical. $R^4$ is, for example, a halogen atom, for example a chlorine, bromine or iodine atom.

(h) for those compounds in which ring X is a thiazole ring, reaction of a compound of the formula XII:

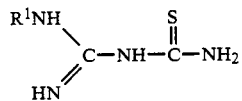

XII with a compound of the formula XIII:

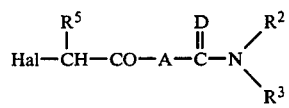

XIII in which Hal is a chlorine or bromine atom and $R^5$ is a hydrogen atom or the optional substituent on the thiazole ring. The reaction may be conducted in a diluent or solvent such as acetone and may be accelerated or completed by the application of heat, for example by heating to the boiling point of the diluent or solvent.

When the process of the invention manufactures the compound of the formula I in the form of the free base and an acid-addition salt is required, the compound of the formula I in the free base form is reacted with an acid which affords a pharmaceutically-acceptable anion.

The starting material of the formula III for use in process (a) may be obtained by separate construction of the two side chains on the appropriate ring X. Thus the left-hand side chain may be constructed by reduction of a nitro group to an amino group, reaction of this amino group with an isothiocyanate of the formula $R^1$—N=C=S, and finally reaction of the resulting thiourea with ammonia in the presence of mercuric oxide. The method of construction of the right hand side chain may vary depending on the nature of ring X, the nature of the atom in ring X to which A is attached (carbon or nitrogen) and the presence or absence of inserted atoms or groups in chain A. In this construction it may be necessary to protect the acid function as a cyano or ester group and to hydroylse to the acid as a final step. When A contains no inserted group or the inserted group is a phenylene radical and Z is a carbon atom, it is preferable to construct the ring X with the right hand chain already in place. Thus when ring X is a thiazole ring a process similar to that described in process (h) may be used, for example as illustrated in Examples 13 and 17. When ring X is a 1,2,3-triazole ring, it may be formed by reaction of methazonic acid with a suitable azide. When ring X is a pyrimidine ring, it may be formed by reaction of a suitably substituted amidine with 2-chloroacrylonitrile, for example as illustrated in Example 2. When the inserted group in A is a vinylene or ethynylene radical, A may be introduced by formation of the double or triple bond by standard coupling methods. When the inserted group in A is a cycloalkylene radical, the chain A may be constructed by a conjugate addition to the corresponding cycloalk-2-enone. When the inserted group in A is an oxygen or sulphur atom or an NH or N-alkyl radical, the right hand chain may be built up by a method similar to that described in process (f), for example as illustrated in Examples 1, 6, 15 and 18. When Z is a nitrogen atom, the right hand chain may be formed by a method similar to that described in process (g), for example as illustrated in Examples 8 and 10.

The starting material of the formula IV for use in process (b) may be prepared by methods exactly analogous to the methods of preparation of the compound of the formula III. Indeed, as already explained, the compound of the formula IV may be an immediate precursor of the compound of the formula III.

The starting material of the formula V for use in process (c) may be prepared by the methods described above for the preparation of the compounds of the formula III or IV in which the right hand chain is constructed first, followed by use of one of the processes (a) or (b).

The cyanamide, corresponding to the amine of the formula V, for use in process (e) may be prepared by reaction of the compound of the formula V with cyanogen bromide.

The starting materials of the formulae VI and VII for use in process (f), and of the formula X for use in process (g) may be prepared by construction of the guanidine chain on a suitably substituted ring X.

The starting material of the formula III for use in process (a) is a particularly useful intermediate for preparing the compounds of the formula I. This starting material, and the activated derivatives (1–6C alkyl ester, acid chloride, acid bromide, mixed anhydride) thereof are therefore provided as a further feature of this invention. Particularly useful mixed anhydrides are those formed with 1–6C alkyl chloroformates, for example ethyl and isobutyl chloroformates.

The starting material of the formula IV for use in process (b) is a particularly useful intermediate for preparing the compounds of the formula I. This starting material is therefore provided as a further feature of the invention.

As noted above, the guanidine derivative of the invention is a histamine H-2 antagonist, inhibits the secretion of gastric acid in warm-blooded animals and is therefore useful in the treatment of peptic ulcers and other conditions caused or exacerbated by gastric acidity, including stress ulcers and gastrointenstinal bleeding due to trauma.

The histamine H-2 antagonist activity may be demonstrated on standard tests, for example by the ability of the compound of the formula I to inhibit the histamine-induced positive chronotropic response in the spontaneously beating right atrium of the guinea pig or by its ability to inhibit the histamine-induced uptake of aminopyrine into the acid space of parietal cells.

The guinea pig atrium test is carried out as follows:

A guinea pig right atrium is suspended at 1 g. tension (isometric) in a thermostatically-controlled (30° C.) tissue bath (25 ml.) containing oxygenated (95% $O_2$, 5% $CO_2$) Krebs-Henseleit buffer (pH 7.4). The tissue is allowed to stabilise over 1 hour during which time it is washed 2—4 times. Individual contractions are recorded with a force-displacement transducer through a strain gauge coupler, and instantaneous rates are monitored with a cardiotachometer. A control response to 1 $\mu$M histamine is obtained after which the tissue is washed 3 times and allowed to re-equilibrate to basal rate. After re-equilibration for 15 minutes, the test compound is added to the desired final concentration. Ten minutes after addition of the compound histamine (1 $\mu$M) is again added and the response to histamine in the presence of antagonist is compared to the histamine control response. The result is expressed as a percentage of the histamine control response. Thereafter the apparent dissociation constant of the H-2 antagonist is determined by standard procedures.

The aminopyrine test is carried out as follows:

Gastric mucosa from the New Zealand white rabbit is removed from the underlying muscle and washed in Buffer 1 [containing per liter NaCl; (8.007 g.), KCl (0.201 g.), $Na_2HPO_4$ (0.113 g.), $KH_2PO_4$ (0.204 g.), $CaCl_2.2H_2O$ (0.132 g.), $MgCl_2$ (0.101 g.) and glucose (1 g.), adjusted to pH 7.4 with NaOH]. The tissue is finely chopped, suspended in Buffer 1 and washed three times with Buffer 1. The tissue is then suspended in dispersion medium [collagenase (Sigma Chemical Co., Type V; 100 mg.) and bovine serum albumin (Miles Laboratories Ltd., Fraction V; 100 mg.) in Buffer 1 (100 ml.); 50 ml. per 10 g. net weight of tissue] and incubated at 30° C. and pH 7.4 (maintained by continuous monitoring) with stirring under an oxygen atmosphere. After 30 minutes the tissue is allowed to settle and the supernatant liquid is removed. Fresh dispersion medium (50 ml. per 10 g. wet weight of tissue) is added and incubation is continued with the tissue being largely dispersed into glands and whole cells after 40-60 minutes. Any remaining large pieces of tissue are removed by filtration through nylon mesh. The mixture of glands and cells is collected by centrifugation at 200×g. and suspended in Buffer 1 containing 1% bovine serum albumin (Miles Laboratories Ltd., Fraction V). Finally the cells and glands are washed 3 times with Buffer 1 and suspended in Buffer 2 [containing Eagles MEM (500 ml.), Aprotinin (Sigma Chemical Co., 10 mg.) and HEPES (2-[4-(2-hydroxyethyl)piperazin-1-yl]ethanesulphonic acid; 150 mM., 20 ml.) adjusted to pH 7.4 with NaOH; 150 ml. per 10 g. net weight of tissue]. The tissue suspension is stirred under an oxygen atmosphere at 32° C. for at least 1 hour before use. The tissue suspension is incubated with the test compound and aminopyrine (10 $\mu$M) labelled with $C^{14}$ on the dimethylamino group (0.1 $\mu$Ci/ml.) for 20 minutes. The uptake of the aminopyrine is then stimulated by addition of histamine and the phosphodiesterase inhibitor ICI 63197 (*Biochem. Soc. Special Publication* 1, 1973, pp 127-132) to final concentrations of $10^{-5}$M. and $5\times10^{-7}$M. respectively. After 18 minutes the cells/glands are separated from the incubation medium by filtration of the suspension through glass microfibre filters. The cells/glands are quickly (<10 seconds) washed three times with ice-cold Buffer 1. The $C^{14}$ aminopyrine retained by the tissue is measured on a scintillation counter and the degree of inhibition of uptake by the test compound is calculated by reference to a control sample. The concentration of test compound giving 50% inhibition is then calculated graphically from a series of tests run at different concentrations.

All the compounds exemplified in this specification were tested either on the guinea pig atrium test or on the aminopyrine test. All those tested on the guinea pig atrium test are active at or below a bath concentration of 10 $\mu$M. and the more active compounds show complete inhibition of response at this concentration. All those tested on the aminopyrine test gave a 50% inhibition of uptake of aminopyrine at or below a concentration of 3 $\mu$M.

The inhibition of the secretion of gastric acid may be demonstrated in standard tests, for example by the ability of the compound of the formula I, when dosed intravenously, intragastrically or orally, to inhibit the secretion of acidic gastric juice in, for example, rats, or dogs provided with gastric fistulae or denervated fundic pouches, and whose gastric secretion is stimulated by administration of a secretagogue, for example histamine, pentagastrin, bethanechol or food.

The test in rats is carried out as follows:

Female rats (200-230 g.) are anesthetized by intramuscular administration of urethane (1.5 g/kg.) and the trachea cannulated. A soft tube is passed down the oesophagus into the stomach and secured by a tie in the neck region. A multi-orifice plastic tube (3 mm. diameter) is passed into the antral region of the stomach, via an incision in the duodenum, and tied in place by means of a ligature around the pylorus. Saline (9 g./l. NaCl) is perfused through the stomach via the oesophageal cannula at a rate of 7 ml./minute and collected into beakers from the pyloric outlet over periods of 10 minutes. Acid secretion is stimulated by subcutaneous administration of the specific H-2 agonist dimaprit in a loading dose of 10 mg./kg. followed by an infusion of 30 mg./kg./hour. Acid output is computed by titration of the 10 minute samples to an end point of pH 6.4 with 20 mM. NaOH. When secretion has reached a plateau (three consecutive readings within 5%) the test compound is administered intravenously via a cannula placed in the left external jugular vein. Secretion is then measured for a further 2 hours. A stock solution of each test compound is prepared (10 mg./ml. in DMSO) and appropriate dilution made with saline to enable the injection in a dose volume of 1 ml./kg. (DMSO <2%).

The test in dogs provided with chronic fistulae is carried out as follows:

A female pure bred beagle (9-12 kg.) having a chronic gastric fistula is fasted overnight with water ad lib. During the experiment the dog is lightly restrained in a standing position. When studying the test compound by the intravenous route, the fistula is opened and, after ascertaining the absence of basal secretion over a period of 30 minutes, a continuous intravenous infusion of secretagogue (0.5 $\mu$mol./kg./hour of histamine or 2 $\mu$g./kg./hour pentagastrin) in saline (15 ml./hour) is begun. Gastric acid samples are collected every 15 minutes. The volume of each sample is measured and a 1 ml. aliquot is titrated to neutrality with 100 mM NaOH to determine acid concentration. When a plateau of secretion is reached (1-2 hours), the test compound is administered intravenously in saline and gastric acid samples are collected for a further 2-3 hours during which time the infusion of the secretagogue continues uninterrupted.

When studying the test compound by the intragastric route, the absence of basal secretion over a period of 30 minutes is ascertained and the test compound, contained in 25 ml. of 0.5% w/v hydroxypropyl methylcellulose and 0.1% w/v 'Tween' 80 in water ('Tween' is a Trade Mark) is instilled into the stomach through a fistula dosing plug. One hour later, the fistula is reopened and intravenous infusion of a secretagogue, as described above, is immediately begun. Gastric acid samples are measured as described above and the approach of acid secretion to a plateau is compared to that of a control animal which is dosed intragastrically only with the dosing vehicle.

When studying the test compound by the oral route it is administered in a gelatin capsule with 15 ml. of water. One hour later, the fistula is opened and intravenous infusion of the secretagogue is immediately begun. Gastric acid samples are measured as above and the approach of acid secretion to a plateau is compared to that of an undosed control animal.

The test in dogs provided with denervated fundic pouches is carried out as follows:

Male beagle dogs (14-22 kg.) are prepared with vagally denervated pouches of the fundic gland area by the method of Rudick et al. (*J. Surg. Res.* 1967, 7 383.) The animals are allowed 4-6 weeks to recover from surgery and a further period of 2-3 months prior to routine use, to allow for table training and standardization of secretory responses. The dogs are starved for 23 hours before use (water ad lib) and during experiments they are lightly restrained in cloth slings. After rinsing the pouch with warm water, histamine is infused subcutaneously at a rate of 10 μg./minute. This dose of agonist produces a submaximal (60-90% of maximum) increase in acid output in all dogs used. Pouch secretions are collected over 15 minute periods into graduated glass test-tubes and the volume measured to the nearest 0.1 ml. A 500 μl sample is diluted with 5 ml. of saline and titrated to pH 7.0 with 100 mM NaOH. Total acid output is computed from the product of acid concentration and volume of juice secreted. Compounds are administered intravenously (0.1 ml./kg.) via a cephalic vein or orally in a gelatin capsule when a secretory plateau (3 consecutive readings within 10%) has been attained. Secretion is measured for a period of 3 hours following administration of test compound.

The results obtained in the atrium and aminopyrine tests are predictive of activity in the rat and dog tests.

No overt toxicity or side effects were noted during the rat or dog tests. The compound 5-[4-(2-allyl-guanidino)-1,2,3-triazol-2-yl]valeramide was administered intravenously to groups of two anaesthetised rats and four conscious mice at doses which were respectively ten times and one hundred times the dose, in mg/kg., which produced an approximate 50% inhibition of gastric secretion in the anaesthetised rat. No toxic symptoms were noted in any of the dosed animals.

The N-methylcyanoguanidine group in known H-2 receptor antagonists is potentially changeable into the carcinogenic N-nitroso N-methylcyanoguanidine group in the mammalian body (Pool et al., *Toxicology*, 1975, 15, 69). The corresponding group in the compounds of the present invention, $CONR^2R^3$, is not potentially changeable into carcinogenic nitroso derivatives when $R^2$ and $R^3$ are hydrogen atoms.

According to a further feature of the invention there is provided a pharmaceutical composition which comprises a guanidine derivative of the invention in association with a non-toxic pharmaceutically-acceptable diluent or carrier.

The pharmaceutical composition may, for example, be in a form suitable for oral, rectal, parenteral or topical administration, for which purposes it may be formulated by means known to the art into the form of, for example, tablets, capsules, aqueous or oily solutions or suspension, emulsions, dispersible powders, suppositories, sterile injectable aqueous or oily solutions or suspensions, gels, creams, ointments or lotions.

In addition to the guanidine derivative of the formula I, the pharmaceutical composition of the invention for oral, rectal or parenteral administration may also contain, or be co-administered with, one or more known drugs selected from antacids, for example aluminium hydroxide-magnesium hydroxide mixtures; antipepsin compounds, for example pepstatin; other histamine H-2 antagonists, for example cimetidine or ranitidine; ulcer healing agents, for example carbenoxolone or bismuth salts; anti-inflammatory agents, for example ibuprofen, indomethacin, naproxen or aspirin prostaglandins, for example 16,16-dimethylprostaglandin $E_2$; classical antihistamines (histamine H-1 antagonists), for example mepyramine or diphenhydramine; anticholinergic agents, for example atropine or propantheline bromide; anxiolytic agents, for example diazepam, chlordiazepoxide or phenobarbital.

The pharmaceutical composition of the invention for topical administration may also contain, in addition to the guanidine derivative, one or more classical anti-histamines (histamine H-1 antagonists), for example mepyramine or diphenhydramine and/or one or more steroidal anti-inflammatory agents, for example fluocinolone or triamcinolone.

A topical formulation may contain 1-10% w/w of the guanidine derivative of the invention. A preferred pharmaceutical composition of the invention is one suitable for oral administration in unit dosage form, for example a tablet or capsule which contains between 5 mg. and 500 mg. of the guanidine derivative, or one suitable for intravenous, subcutaneous or intramuscular injection, for example a sterile injectable containing between 0.1% and 10% w/w of the guanidine derivative.

The pharmaceutical composition of the invention will normally be administered to man for the treatment of peptic ulcers and other conditions caused or exacerbated by gastric acidity in the same general manner as that employed for cimetidine, due allowance being made in terms of dose levels for the potency and duration of action of the guanidine derivative of the present invention relative to cimetidine. Thus each patient will receive an oral dose of between 15 mg. and 1500 mg., and preferably between 20 mg. and 200 mg., of guanidine derivative or an intravenous, subcutaneous or intramuscular dose of between 1.5 mg. and 50 mg., and preferably between 5 mg. and 20 mg., of the guanidine derivative, the composition being administered 1 to 4 times per day. The rectal dose will be approximately the same as the oral dose. The composition may be administered less frequently when it contains an amount of guanidine derivative which is a multiple of the amount which is effective when given 1-4 times per day.

The invention is illustrated, but not limited, by the following Examples. The n.m.r. spectra are quoted in δ relative to tetramethylsilane (δ=O) as internal standard (s=singlet, d=doublet, t=triplet, q=quartet, m=multiplet, br=broad). The temperatures are in degrees Centigrade. The following contractions are used:

HOAc=acetic acid,
DMF=dimethyl formamide,
ether=diethyl ether,
DMSO=dimethylsulphoxide,
MeOH=methanol,
EtOH=ethanol,
THF=tetrahydrofuran,
EtOAc=ethyl acetate.

Attention is drawn to the fact that 3-nitropyrazole (Example 10) and 4-nitrotriazole (Example 8) are both explosion hazards.

EXAMPLE 1

A mixture of 4-(4-[2-propylguanidino]pyrimid-2-ylthio)butyronitrile (0.18 g.) and concentrated sulphuric acid (1.5 ml.) was stirred at ambient temperature for 2.5 hours. The reaction mixture was cooled in an ice-bath and basified by careful dropwise addition of concentrated aqueous ammonia (s.g. 0.880). The resulting white precipitate was collected, washed with water and allowed to dry. The solid was purified by preparative t.l.c. using Merck silica 60F254 and $CHCl_3$/MeOH/aqueous ammonia (s.g. 0.880) 8:2:0.3 v/v/v as eluant. The purified product was converted in EtOH solution to the maleate salt to give 4-(4-[2-propylguanidino]-pyrimid-2-ylthio)butyramide maleate (0.10 g.) m.p. 200°-202°.

The starting material may be obtained as follows:

4-Chlorobutyronitrile (0.23 g.) in EtOH (2 ml.) was added to a solution of 2-thiocytosine (0.25 g.) in 0.5N aqueous NaOH (5 ml.) and the mixture stirred for 18 hours. A further portion of 4-chlorobutyronitrile (0.23 g.) was added and the mixture stirred a further 24 hours. The solution was concentrated in vacuo to 2 ml. and cooled and the crystalline precipitate collected to give 4-[4-aminopyrimid-2-ylthio]butyronitrile (0.3 g.) m.p. 99°-100°.

A mixture of 4-[4-aminopyrimid-2-ylthio]butyronitrile (0.75 g.), n-propylisothiocyanate (0.8 g.) and pyridine (5 ml.) was heated at 130° for 2 hours and then heated under reflux for 18 hours. The solvent was removed by evaporation in vacuo and the residual oil was purified by medium pressure chromatography on silica using $CHCl_3$/MeOH 9.75:0.25 v/v as eluant. A portion of the purified product (0.3 g.) and EtOH (5 ml.) was added to EtOH saturated with ammonia (10 ml.) and mercuric oxide (0.22 g.). After 15 minutes the reaction mixture was filtered through diatomaceous earth and the filtrate was evaporated to give a white semi-crystalline solid which was purified by medium pressure chromatography on silica using $CHCl_3$/MeOH/aqueous ammonia (s.g. 0.880) 9:1:0.1 v/v/v as eluant. There was thus obtained 4-(4-[2-propylguanidino]pyrimid-2-ylthio]butyronitrile (0.18 g.) which was used without further purification.

EXAMPLE 2

A mixture of 5-(4-[2-propylguanidino]pyrimid-2-yl)valeronitrile (0.25 g.) and concentrated sulphuric acid (2 ml.) was stirred at ambient temperature for 3.5 hours. The reaction mixture was cooled in an ice bath and basified by careful dropwise addition of concentrated aqueous ammonia (s.g. 0.880). The resulting white precipitate was collected, washed with water and allowed to dry. The solid was purified by medium pressure chromatography on silica gel using $CHCl_3$/MeOH/aqueous ammonia (s.g. 0.880) 8:2:0.3 v/v/v as eluant to give 5-(4-[2-propylguanidino]pyrimid-2-yl)valeramide (0.15 g.), m.p. 212°-214°.

The starting material may be prepared as follows:

A mixture of ethyl 5-cyanovalerimidate (21 g.) and ammonium chloride (7.5 g.) in MeOH (100 ml.) was stirred overnight at room temperature and then evaporated to dryness. The residue was heated under reflux in EtOH (150 ml.) with triethylamine (56 g.) and 2-chloroacrylonitrile (36 g.). After 2 hours the mixture was evaporated to dryness and the residue was then stirred in water (300 ml.) containing sufficient HOAc to give a pH of 4. Charcoal was added and after 30 minutes the mixture was filtered and the aqueous solution extracted with EtOAc (2×150 ml.). The aqueous layer was basified with aqueous sodium hydroxide to pH 10 and extracted with EtOAc (3×150 ml.). The combined extracts were evaporated to dryness and the residue recrystallised from acetonitrile to give 2-(4-cyanobutyl)-4-aminopyrimidine.

A mixture of 2-(4-cyanobutyl)-4-aminopyrimidine (1.0 g.), n-propylisothiocyanate (0.57 g.) and pyridine (25 ml.) was heated under reflux for 3 hours. The solvent was removed by evaporation in vacuo and the residue was purified by medium pressure chromatography on silica gel using $CHCl_3$/MeOH 9.75:0.25 v/v as eluant. The purified product (0.85 g.) in EtOH (10 ml.) was added to EtOH saturated with ammonia (30 ml.) and mercuric oxide (0.6 g.). After 15 minutes the reaction mixture was filtered through diatomaceous earth and the filtrate was evaporated to give 5-(4-[2-propylguanidino]pyrimid-2-yl)valeronitrile (0.85 g.) which was used without further purification.

EXAMPLES 3-5

The process of Example 1 was repeated using the appropriate starting materials to give the following compounds:

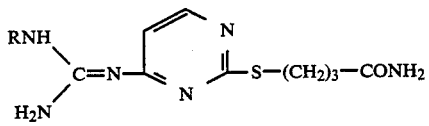

| Example | R | Salt | m.p. ° | Yield % |
|---|---|---|---|---|
| 3 | $CH_3$ | maleate | 207-208 | 48 |
| 4 | $i-C_3H_7$ | maleate | 178-179 | 40 |
| 5 | $C_2H_5$ | — | 180-182 | 32 |

The starting material may be prepared by repeating the third part of Example 1 using the appropriate isothiocyanate in place of n-propylisothiocyanate.

EXAMPLE 6

A solution of 4-[2-(3-ethylthioureido)pyrid-6-ylthio]butyramide (0.25 g.) in methanolic ammonia was treated with yellow mercuric oxide (0.5 g.) and the mixture stirred at room temperature for three hours. The mixture was filtered and the filtrate evaporated to dryness. A solution of the residue in acetone was added to a solution of maleic acid in acetone and the crystalline precipitate collected to give 4-[2-(2-ethylguanidino)pyrid-6-ylthio]butyramide hydrogen maleate (0.22 g.), m.p. 174°-176°.

The starting material may be prepared as follows:

A mixture of sodium (1.84 g.), EtOH (100 ml.) and 4-mercaptobutyric acid (5.28 g.) was heated to reflux and then treated with 2,6-dibromopyridine (9.5 g.), and the mixture heated under reflux for 18 hours and then evaporated to dryness. The residue was partitioned between water and ether and the aqueous phase was acidified with HOAc and extracted with ether. The ether extract was dried and evaporated to dryness to give 4-(2-bromopyrid-6-ylthio)butyric acid (9.5 g.), m.p. 72°-74°.

A mixture of 4-(2-bromopyrid-6-ylthio)butyric acid (7 g.) and thionyl chloride (35 ml.) was heated under reflux for 1 hour and then evaporated to dryness. The residue was treated with concentrated aqueous ammonia (70 ml.) and the mixture stirred vigorously for 2 hours. The insoluble solid was collected to give 4-(2-bromopyrid-6-ylthio)butyramide, m.p. 87°-88°.

A mixture of 4-(2-bromopyrid-6-ylthio)butyramide (5 g.) and concentrated aqueous ammonia (25 ml.) was heated in a sealed tube at 180° for 24 hours. The mixture was cooled and diluted with water, and then extracted twice with EtOAc. The combined extracts were extracted twice with N aqueous HCl and the aqueous acid extracts were combined, basified with 10N aqueous NaOH, and extracted with EtOAc. The EtOAc extract was dried and evaporated to dryness to give 4-(2-aminopyrid-6-ylthio)butyramide.

A mixture of 4-(2-aminopyrid-6-ylthio)butyramide (0.25 g.), ethylisothiocyanate (0.2 g.) and acetonitrile (5 ml.) was heated under reflux for 18 hours and then cooled, and the solid which crystallised was collected to give 4-[2-(3-ethylthioureido)pyrid-6-ylthio]butyramide (0.25 g.) which was used without further purification.

EXAMPLE 7

The process of Example 6 was repeated using the appropriate starting material to give 4-[2-(2-propylguanidino)pyrid-6-ylthio]butyramide hydrogen maleate (yield 15%), m.p. 138°–140°.

The starting material may be obtained by repeating the last part of Example 6, using n-propylisothiocyanate in place of ethylisothiocyanate.

EXAMPLE 8

A stirred mixture of unpurified 5-(4-[3-allylthioureido]-1,2,3-triazol-2-yl)valeramide (0.09 g.), yellow mercuric oxide (0.13 g.) and ammoniacal EtOH (6M; 10 ml.) was kept at room temperature for 3 hours. The mixture was filtered, evaporated, and the residue redissolved in a small volume of EtOAc/MeOH. This solution was treated with a solution of maleic acid (0.037 g.) in a small volume of acetone and then diluted with ether to give 0.07 g. of 5-(4-[2-allylguanidino]-1,2,3-triazol-2-yl)valeramide maleate, m.p. 116°–118°.

The starting material may be obtained as follows:

A stirred solution of 4-nitro-1,2,3-triazole (23.0 g.) in dry DMF (135 ml.) was treated at room temperature with a dispersion of sodium hydride (4.8 g.) in mineral oil (4.8 g.). The mixture was stirred for 30 minutes and then treated with 5-bromovaleronitrile (33.0 g.). The mixture was stirred overnight at room temperature and then poured into water. The product was extracted into EtOAc and purified by column chromatography on silica gel (1 kg.) eluted with EtOAc/petroleum ether (b.p. 60°–80°) 1:1 v/v to give 22.3 g. of 5-(4-nitro-1,2,3-triazol-2-yl)valeronitrile as an oil.

A mixture of 5-(4-nitro-1,2,3-triazol-2-yl)valeronitrile (2.0 g.) and concentrated sulphuric acid (2 ml.) was kept at room temperature for 5 hours. The mixture was poured into ice-water and basified with aqueous NaOH. The mixture was saturated with NaCl and extracted with EtOAc. The extract was dried (MgSO$_4$) and evaporated to give 1.65 g. of unpurified 5-(4-nitro-1,2,3-triazol-2-yl)valeramide.

A stirred mixture of unpurified 5-(4-nitro-1,2,3-triazol-2-yl)valeramide (1.65 g.), palladium on charcoal (5% w/w; 0.8 g.), and HOAc was kept at room temperature under one atmosphere of hydrogen until 610 ml. of hydrogen had been absorbed. The mixture was filtered and evaporated. The residue was triturated with hot isopropanol and filtered to give 0.4 g. of 5-(4-amino-1,2,3-triazol-2-yl)valeramide, m.p. 147°–148°.

A mixture of 5-(4-amino-1,2,3-triazol-2-yl)valeramide (0.18 g.), allylisothiocyanate (0.11 g.), and DMF (5 ml.) was stirred at room temperature overnight. The mixture was poured into water and extracted with EtOAc. The extract was dried (MgSO$_4$) and evaporated to give 0.09 g. of 5-(4-[3-allylthioureido]-1,2,3-triazol-2-yl)valeramide which was used without further purification.

EXAMPLE 9

A mixture of 5-(4-[2-allylguanidino]-1,2,3-triazol-2-yl)valeramide maleate (0.11 g.), PtO$_2$ (0.08 g.), EtOH (5 ml.) and DMF (1 ml.) was stirred at room temperature under one atmosphere of hydrogen until 60 ml. of hydrogen had been absorbed. The mixture was filtered and evaporated to give an oil that was partitioned between EtOAc and aqueous NaHCO$_3$. The organic phase was dried (MgSO$_4$) and evaporated to give a portion of the product. The aqueous phase was saturated with NaCl, evaporated to dryness, stirred overnight and acetonitrile, and filtered to give a solution of a second portion of the product. The two portions of product were combined, the solvent evaporated, and the residue redissolved in a small volume of MeOH/EtOAc. This solution was treated with a solution of maleic acid (0.03 g.) in a small volume of acetone and then diluted with ether to precipitate an oil, which slowly solidified. The solidified oil was filtered and washed with ether to give 0.07 g. of 5-(4-[2-propylguanidino]-1,2,3-triazol-2-yl)valeramide maleate hemihydrate, m.p. 67°–69°.

EXAMPLE 10

A mixture of 5-(3-[2-propylguanidino]pyrazol-1-yl)valeronitrile (1.1 g.) and concentrated sulphuric acid (3 ml.) was stirred for 18 hours at room temperature. The solution was added to ice-water and basified with 10N aqueous NaOH. Extraction with EtOAc and work up gave a brown impure oil which was converted in acetone to the maleate salt. Crystallisation was induced by addition of a small volume of ether to give 5-(3-[2-propylguanidino)pyrazol-1-yl)valeramide hydrogen maleate (0.45 g.), m.p. 132°–134° (yield 26%).

The starting material may be prepared as follows:

Sodium hydride paste (6.16 g. of 61% w/w suspension in liquid paraffin) was added portionwise over 30 minutes to a solution of 3-nitropyrazole (17.4 g.) in dry DMF (150 ml.) with external ice cooling to maintain the temperature at 20°–30°. The mixture was stirred for 45 minutes and to the almost clear solution was added 5-bromovaleronitrile (25 g.) over 30 minutes, at 25°–30°, and the mixture was stirred for 4 hours. Water (450 ml.) and EtOAc (450 ml.) were added and the upper layer was separated, dried (MgSO$_4$) and evaporated in vacuo to an oil which was a mixture of 5-(3-nitropyrazol-1-yl)valeronitrile and 5-(5-nitropyrazol-1-yl)valeronitrile. The oil was divided into two 15 g. portions which were fractionated on a silica column (3.5 cm diameter × 100 cm long) eluted at 2 atmospheres by EtOAc/60°–80° petroleum ether (3:7 v/v). The 1,5 isomer was eluted first followed by the 1,3 isomer. The 5-(3-nitropyrazol-1-yl)valeronitrile had m.p. 32°–33°.

To a solution of 5-(3-nitropyrazol-1-yl)valeronitrile (9.16 g.) in dry THF (200 ml.) was added 5% w/w palladium on carbon (1.8 g.). The mixture was stirred at 20° under an atmosphere of hydrogen. 3.2 Liters of hydrogen were absorbed over 4 hours. The catalyst was filtered off and the filtrate was evaporated in vacuo to give 5-(3-aminopyrazol-1-yl)valeronitrile as an oil.

A solution of 5-(3-aminopyrazol-1-yl)valeronitrile (1.0 g.) in acetonitrile (10 ml.) was treated with n-propylisothiocyanate (0.74 g.) and the solution heated under reflux on the steam bath for 6 hours. Evaporation of the solvent gave a brown gum which on trituration with ether/EtOH gave 5-(3-[3-propylthioureido]pyrazol-1-yl)valeronitrile as a white solid (1.01 g.).

A solution of 5-(3-[3-propylthioureido]pyrazol-1-yl)valeronitrile (1.01 g.) in saturated methanolic ammonia (30 ml.) was treated with orange mercuric oxide (0.82 g.) and the suspension stirred at room temperature for 18 hours. The black suspension was filtered through diatomaceous earth and the filtrate evaporated to give 5-(3-[2-propylguanidino]pyrazol-1-yl)valeronitrile as a brown oil which was used without further purification.

EXAMPLES 11-12

The process of Example 10 was repeated using the appropriate starting materials to give 5-[3-(2-methylguanidino)pyrazol-1-yl]valeramide 1.25 maleate (yield 14%) [n.m.r. in d$_6$DMSO: 1.8 (m, 4H); 2.3 (t, 2H); 3.1 (s, 3H); 4.3 (t, 2H); 6.2 (d, 1H); 6.3 (s, 2.5H); 7.95 (d, 1H)] and 5-[3-(2-ethylguanidino)pyrazol-1-yl]valeramide maleate, m.p. 132°-134° (yield 23%).

The starting materials may be prepared by repeating the fourth and fifth parts of Example 10 using methylisothiocyanate and ethylisothiocyanate respectively in place of n-propylisothiocyanate.

EXAMPLE 13

A solution of methyl 3-[2-(2-methylguanidino)-thiazol-4-yl]benzoate hydrochloride (1 g.) in ethanolic methylamine (30% w/v) was allowed to stand at room temperature for 4 days and then evaporated to dryness. The residue was recrystallised from MeOH to give 0.27 g. of N-methyl-3-[2-(2-methylguanidino)thiazol-4-yl]benzamide, m.p. 111°-113° (yield 30%).

The starting material may be prepared as follows:

A solution of 3-cyanophenacylchloride (3.6 g.), in EtOH (30 ml.) was added to methylamidinothiourea (2.65 g.) in EtOH (30 ml.) and the mixture was heated under reflux for 1 hour. The crystalline product was filtered off and washed with EtOH. A solution of this material (3.5 g.) in a mixture of concentrated aqueous hydrochloric acid (40 ml.) and HOAc (40 ml.) was heated under reflux for 16 hours. The mixture was evaporated to dryness and the residue in MeOH (100 ml.) treated with thionyl chloride (15 ml.). The mixture was stirred for 2 hours and then evaporated to dryness. The residue was triturated with acetonitrile to give methyl 3-[2-(2-methylguanidino)thiazol-4-yl]benzoate hydrochloride, having the following n.m.r. in d$_6$DMSO: 3.1 (d, 3H); 4.0 (s, 3H); 6.7 (s, 2H); 7.6 (s, 2H); 7.8-8.6 (m, 5H).

EXAMPLE 14

The process of Example 13 was repeated using 1,2-ethylene diamine in place of methylamine to give N-(2-aminoethyl)-3-[2-(2-methylguanidino)thiazol-4-yl]benzamide m.p. 214°-216° (yield 32%).

EXAMPLE 15

To methyl 3-[2-guanidinothiazol-4-ylmethylthio]propionate (0.775 g.), in MeOH (10 ml.) was added hydrazine hydrate (2 ml.; 64% w/v) and the solution stirred at room temperature for 18 hours. The resulting suspension was filtered and the filtrate crystallised from MeOH to give 3-[2-guanidinothiazol-4-ylmethylthio]-propionylhydrazide as a white solid (0.23 g.), m.p. 185°-187°.

The starting material may be prepared as follows:

To 2-guanidino-4-chloromethylthiazole hydrochloride (3.86 g.) and methyl 3-mercaptopropionate (3.0 g.) in EtOH (45 ml.) at 0° was added sodium hydroxide (1.6 g.) in water (15 ml.) over 15 minutes. The reaction mixture was allowed to attain room temperature and to stand for 18 hours. The solution was poured into water and extracted with EtOAc. The extract was washed with aqueous sodium hydroxide solution, water, dried and evaporated to give methyl 3-(2-guanidinothiazol-4-yl-methylthio)propionate as a yellow oil which was used without further purification.

EXAMPLE 16

Methyl 3-(2-guanidinothiazol-4-yl)cyclopentane carboxylate (0.40 g.) and a solution of methylamine in EtOH (33% w/v; 15 ml.) was allowed to stand at ambient temperature for 60 hours. The solvent was removed by evaporation in vacuo and the residue was purified by medium pressure chromatography on silica gel using CHCl$_3$/MeOH/aqueous ammonia (s.g. 0.88) 8:2:0.3 v/v/v as eluant to give N-methyl-3-(2-guanidino-thiazol-4-yl)cyclopentane carboxamide (0.27 g.), m.p. 216°-218°.

The starting material may be prepared as follows:

A mixture of 3-methoxycarbonyl-1-chloroacetylcyclopentane (1.02 g.) and amidinothiourea (0.6 g.) in MeOH (10 ml.) was heated under reflux for 1 hour. The solvent was removed by evaporation in vacuo and the residue was purified by low pressure chromatography on silica gel using CHCl$_3$/MeOH/aqueous ammonia (s.g. 0.880) 9:1.5:0.1 v/v/v as eluant. The product was triturated with ether to give methyl 3-(2-guanidino-thiazol-4-yl)cyclopentane carboxylate (1.14 g.), m.p. 124°-126°.

EXAMPLE 17

A solution of 3-[2-guanidinothiazol-4-yl]benzonitrile (0.5 g.) in a mixture of HOAc (10 ml.) and concentrated aqueous hydrochloric acid (20 ml.) was heated at 90° for 6 hours. The mixture was then evaporated to dryness and the residue dissolved in MeOH (15 ml.) and thionyl chloride (3 ml.) added dropwise. After stirring at ambient temperature for 2 hours the mixture was heated under reflux and then allowed to cool. The crystalline ester was filtered off and stirred in a solution of methylamine in EtOH (30% w/v; 25 ml.) for 4 days at ambient temperature. The mixture was evaporated to dryness and the residue purified by medium pressure liquid chromatography on silica gel using chloroform/MeOH/aqueous ammonia (s.g. 0.880) 9:1:0.5 v/v/v as eluant to give 0.04 g. of N-methyl-3-[2-guanidino-thiazol-4-yl]benzamide m.p. 232°-235° (yield 7%).

The starting material may be prepared as follows:

A mixture of 3-cyanophenacyl chloride (1.78 g.) and amidinothiourea (1.2 g.) in EtOH (40 ml.) was heated under reflux for 1 hour. The solid precipitate was filtered off, dissolved in hot water (100 ml.) and the solution basified with sodium bicarbonate. The precipitated solid was filtered off and dried to give 3-[2-guanidinothiazol-4-yl]benzonitrile which was used without further purification.

EXAMPLE 18

A solution of 4-[2-(2-t-butylguanidino)pyrid-6-yl thio]butyronitrile hydrogen maleate (0.1 g.) in concentrated sulphuric acid (0.5 ml.) was kept at room temperature for 72 hours. The solution was added to crushed ice and then basified with 10N aqueous NaOH and the mixture extracted three times with EtOAc. The combined extracts were dried and evaporated to dryness. A solution of the residue in acetone was added to a solution of maleic acid in acetone, and the crystalline precipitate was collected to give 4-(2-guanidinopyrid-6-ylthio)butyramide hydrogen maleate (0.04 g.), m.p. 169°-170°.

The starting material may be prepared as follows:

2-Amino-6-bromopyridine (40 g.) was added to a solution of benzyl mercaptan (83.7 ml.) and sodium (16.4 g.) in EtOH and the mixture stirred and heated under reflux for 72 hours. The mixture was evaporated to dryness and the residue stirred with a mixture of water (1.4 l.) and EtOAc (700 ml.) and acidified to pH 1 with concentrated aqueous hydrochloric acid. The precipitated solid was collected to give 2-amino-6-benzylthiopyridine hydrochloride (30 g.), m.p. 189°-191°.

A solution of 2-amino-6-benzylthiopyridine hydrochloride (47.2 g.) in liquid NH₃ (700 ml.) was stirred while Na (17.0 g.) was added in small portions. When the addition was complete NH₄Cl (21.9 g.) was added and then the mixture was evaporated to dryness. The residue was dissolved in a mixture of EtOH (100 ml.) and H₂O (100 ml.) and the mixture treated with 4-bromobutyronitrile (23 ml.) and stirred at room temperature for 18 hours. Ths solution was evaporated to dryness and the residue was partitioned between 2N aqueous HCl and ether. The aqueous phase was basified with 10N aqueous NaOH and extracted with EtOAc. The extract was dried over Na₂SO₄ and evaporated to dryness to give 4-(2-aminopyrid-6-ylthio)butyronitrile (36.1 g.) which was used without further purification.

A solution of 4-(2-aminopyrid-6-ylthio)butyronitrile (0.39 g.) and t-butylisothiocyanate (0.25 g.) in THF (10 ml.) was stirred under an argon atmosphere while adding a solution of n-butyl lithium in hexane (1.55M; 2 ml.). The mixture was stirred at room temperature for three hours and then evaporated to dryness. The residue was partitioned between EtOAc and water and the EtOAc phase was dried and evaporated to dryness. The residue was recrystallised from EtOH to give 4-[2-(3-t-butylthioureido)pyrid-6-ylthio]butyronitrile (0.32 g.), m.p. 156°-157°.

A solution of 4-[2-(3-t-butylthioureido)pyrid-6-ylthio]butyronitrile (0.25 g.) in methanolic ammonia was treated with yellow mercuric oxide (0.3 g.) and the mixture was stirred at room temperature for four hours and then filtered. The filtrate was evaporated to dryness and the residue partitioned between N aqueous hydrochloric acid and ether. The aqueous phase was basified with 10N aqueous NaOH and extracted with EtOAc and the extract was dried and then evaporated to dryness. A solution of the residue in acetone was added to a solution of maleic acid in acetone, and the solution was diluted with ether. The crystalline precipitate was collected to give 4-[2-(2-t-butylguanidino)pyrid-6-ylthio]butyronitrile hydrogen maleate (0.22 g.), m.p. 146°-147°.

EXAMPLE 19

A tablet containing 100 mg. of 4-(4-[2-propylguanidino]pyrimid-2-ylthio)butyramide may be prepared using ingredients in the following proportions:

|     |                              | mg./tablet |
| --- | ---------------------------- | ---------- |
| (a) | Tablet Core.                 |            |
|     | Active agent                 | 200        |
|     | Lactose                      | 68.5       |
|     | Calcium carboxymethylcellulose | 22.5     |
|     | Polyvinylpyrrolidone         | 6.0        |
|     | Magnesium stearate           | 3.0        |
| (b) | Tablet Coat                  |            |
|     | Hydroxypropylmethylcellulose | 4.5        |
|     | Polyethylene glycol          | 0.9        |
|     | Titanium dioxide             | 1.35       |

The active agent, lactose and calcium carboxymethylcellulose are mixed. An aqueous solution of polyvinylpyrrolidone is added, and the mass is then mixed until it is suitable for granulation. The mass is then granulated and dried. The magnesium stearate is blended with the dried granules and the resulting mixture is compressed into tablets. The tablets are film-coated using an aqueous or solvent suspension of hydroxypropylmethylcellulose, polyethylene glycol and titanium dioxide.

We claim:
1. A guanidine compound of the formula I:

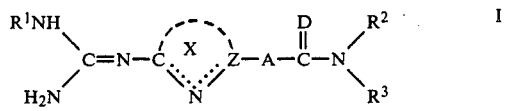

in which

R¹ is a hydrogen atom or a 1-10C alkyl, 3-8C cycloalkyl, 4-14C cycloalkylalkyl, 3-6C alkenyl, 3-6C alkynyl, 1-6C alkanoyl, phenyl, 7-11C phenylalkyl or benzoyl radical, the phenyl, phenylalkyl and benzoyl radicals being optionally substituted on the phenyl ring by one or two substituents selected from halogen atoms and 1-6C alkyl, 1-6C alkoxy, 1-6C alkylthio, trifluoromethyl, hydroxy and amino radicals;

in ring X the dotted line is a double bond on one side of the nitrogen atom and Z is a carbon or nitrogen atom such that ring X is a 5-membered aromatic heterocyclic ring which contains at least one nitrogen atom and may optionally contain one or two additional hetero atoms selected from oxygen, nitrogen and sulphur atoms, which heterocyclic ring may, where possible, carry one or two optional substituents, the optional substituents on ring X being selected from fluorine, chlorine and bromine atoms and 1-6C alkyl, 1-6C alkoxy, trifluoromethyl, hydroxy and amino radicals;

A is a phenylene or 5-7C cycloalkylene radical or a 1-8C alkylene chain which is optionally substituted by one or two 1-3C alkyl radicals and into which is optionally inserted, as part of the backbone of the chain, one or two groups selected from oxygen and sulphur atoms and NH, 1-6C N-alkyl, cis and trans vinylene, ethynylene, phenylene and 5-7C cycloalkylene radicals, provided that the shortest link between ring X and C=D is of at least 3 atoms, provided that when an optional insertion is made in chain A which results in the inserted group being directly attached to C=D the inserted group is other than an oxygen or sulphur atom or an NH or N-alkyl radical, and provided that no two insertions selected from oxygen and sulphur atoms and NH and N-alkyl radicals are directly attached one to the other;

D is an oxygen or sulphur atom;

R² is a hydrogen atom or a hydroxy, amino, 1-6C alkylamino, 1-6C haloalkylamino, 1-6C alkanoylamino, 1-6C alkyl, 3-8C cycloalkyl, 4-12C cycloalkylalkyl, 2-6C alkenyl, 2-6C alkynyl, 1-6 haloalkyl, 1-6C alkoxy, 1-6C hydroxyalkyl, 2-10C alkoxyalkyl, 2-10C alkylthioalkyl, 1-6C aminoalkyl, 2-8C alkylaminoalkyl, 3-12C dialkylaminoalkyl, 2-8C alkanoylaminoalkyl, 8-14C benzoylaminoalkyl 3-10C alkoxycarbonylalkyl, 2-8C carbamoylalkyl, phenyl, 7-11C phenylalkyl, heteroaryl or heteroarylalkyl radicals, wherein the heteroaryl part is a heterocyclic aromatic ring containing one, two or three heteroatoms selected from oxygen, nitrogen and sulphur atoms, wherein the alkyl part of the heteroarylalkyl radical is 1-6C and wherein, when $R^3$ is or contains an aryl or heteroaryl ring, that ring is optionally substituted by one or two groups selected from flourine, chlorine, bromine and iodine atoms and 1-6C alkyl, 1-6C alkoxy, 1-6C alkylthio, 2-6C dialkylamino, 2-6C alkanoyl, trifluoromethyl, hydroxy and amino radicals;

$R^3$ is a hydrogen atom or $R^2$ and $R^3$ and the nitrogen atom to which they are attached together form a 5-, 6- or 7-membered saturated ring which optionally contains a double bond, or in which ring one carbon atom is replaced by oxygen, NH or NR wherein R is a 1-6C alkyl radical; provided that when $R^1$ is a hydrogen atom or an alkyl radical, ring X is a thiazole ring in which A is attached at the 4-position and A is an alkylene chain which has a single optional insertion of a sulphur atom, then $NR^2R^3$ is other than $NH_2$, NHOH or NH alkyl: and the pharmaceutically-acceptable acid-addition salts thereof.

2. A guanidine compound of the formula I given in claim 1 in which $R^1$ is a hydrogen atom or a methyl, ethyl, propyl, isopropyl, butyl, cyclohexyl, cyclohexylmethyl, allyl, propargyl, acetyl, phenyl, benzyl or benzoyl radical, the phenyl, benzyl and benzoyl radicals being optionally substituted on the benzene ring by one or two substituents selected from fluorine, chlorine and bromine atoms and methyl, methoxy, methylthio, trifluoromethyl, hydroxy and amino radicals;

ring X is an oxazole, thiazole, imidazole, 1,2,4-thiadiazole, 1,2,4-oxadiazole, 1,2,3-triazole, 1,2,4-triazole or, pyrazole, ring, ring X being optionally substituted, where possible, by one or two substituents selected from fluorine, chlorine and bromine atoms and methyl, methoxy, methylthio, trifluoromethyl, hydroxy and amino radicals;

—A— is a phenylene, cyclopentylene, cyclohexylene, trimethylene, tetramethylene, pentamethylene, thioethylene, thiotrimethylene, thiotetramethylene, thiopentamethylene, oxyethylene, oxytrimethylene, oxytetramethylene, methylenethiomethylene, methylenethioethylene, methylenethiopropylene, methyleneoxymethylene, methyleneoxyethylene, ethyleneoxyethylene, oxy-2-methylethylene, thiopropylenethiomethylene, oxyethyleneoxymethylene, iminopropylene, iminoethylene, vinylenepropylene, oxymethylene-vinylene, 1,3-phenylene, 1,3-cyclopentylene, methylene-b 1,4-phenylene, ethyleneoxymethylene-1,4-phenylene, oxy-1,3-phenylenemethylene or thiomethylene-ethynylenemethylene radical;

D is an oxygen or sulphur atom;

$R^2$ is a hydrogen atom or a hydroxy, amino, methylamino, 2,2,2,-trifluoroethylamino, acetylamino, methyl, cyclohexyl, cyclohexylmethyl, allyl, propargyl, 2,2,2-trifluoroethyl, methoxy, 2-hydroxyethyl, 2-methoxyethyl, 2-methylthioethyl, 2-aminoethyl, 2-methylaminoethyl, 2-dimethylaminoethyl, 2-acetylaminoethyl, 2-benzoylaminoethyl, methoxycarbonylmethyl, 2-carbamoylpropyl, phenyl, benzyl, heteroaryl and heteroarylmethyl wherein the heteroaryl part is a furan, thiophene, pyrrole, thiazole, oxazole, imidazole, thiadiazole, oxadiazole, triazole, pyrazole, pyridine or pyrimidine ring and wherein when $R^2$ is or contains a phenyl or heteroaryl ring that ring is optionally substituted by one or two groups selected from fluorine, chlorine, bromine and iodine atoms and methyl, methoxy, methylthio, dimethylamino, acetyl, trifluoromethyl, hydroxy and amino radicals;

$R^3$ is a hydrogen atoms, or $R^2$ and $R^3$ are joined to form, together with the nitrogen atom to which they are attached, a pyrrolidine, piperidine, morpholine, piperazine or N-methylpiperazine ring;

provided that when $R^1$ is a hydrogen atom or a methyl, ethyl, propyl, isopropyl or butyl radical, ring X is a thiazole ring in which A is attached at the 4-position and A is a trimethylene, tetramethylene, pentamethylene, thioethylene, thiotrimethylene, thiotetramethylene, thiopentamethylene, methylenethiomethylene, methylenethioethylene or methylenethiopropylene radical, then $NR^2R^3$ is other than $NH_2$, NHOH or $NHCH_3$: and the pharmaceutically-acceptable acid-addition salts thereof.

3. A guanidine compound as claimed in claim 1 or 2 in which D is an oxygen atom and $R^2$ and $R^3$ are hydrogen atoms.

4. A guanidine compound as claimed in any of claims 1, 2, or 3 in which $R^1$ is a methyl, ethyl, propyl, isopropyl or alkyl radical.

5. A guanidine compound as claimed in any of claims 1, 2, 3 or 4 in which ring X, which carries no optional substituent, is a pyrazole in which A is attached at the 2-position, or 1,2,3-triazole ring.

6. A guanidine compound as claimed in any of claims 1, 2, 3 or 4 in which ring X is a pyrazole, or 1,2,3-triazole ring and A is a tetramethylene radical.

7. A guanidine compound selected from the group consisting of 4-(4-[2-isopropylguanidino]pyramid-2-ylthio)butyramide, 4-(6-[2-propylguanidino]pyrid-2-ylthio)butyramide, 5-(4-[2-allylguanidino]-1,2,3-triazol-2-yl)valeramide, 5-(4-[2-propylguanidino]-1,2,3-triazole-2-yl)valeramide, 5-(3-[2-propylguanidino]-pyrazole-1-yl)valeramide and the pharmaceutically-acceptable acid-addition salts thereof.

8. A pharmaceutical composition which comprises a guanidine compound as claimed in claim 1 in association, in an amount effective to inhibit gastric acid secretion, with a pharmaceutically-acceptable diluent or carrier.

9. A method of inhibiting gastric acid secretion in a living animal comprising administering to the animal the composition of claim 8.

* * * * *